(12) United States Patent
Chuang et al.

(10) Patent No.: US 10,337,017 B2
(45) Date of Patent: Jul. 2, 2019

(54) METHOD OF STIMULATING TLR9-ACTIVATED IMMUNE RESPONSE

(71) Applicant: NATIONAL HEALTH RESEARCH INSTITUTES, Miaoli County (TW)

(72) Inventors: Tsung-Hsien Chuang, Miaoli County (TW); Chao-Yang Lai, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 15/859,022

(22) Filed: Dec. 29, 2017

(65) Prior Publication Data

US 2018/0135053 A1 May 17, 2018

Related U.S. Application Data

(63) Continuation of application No. 14/906,150, filed as application No. PCT/US2014/047271 on Jul. 18, 2014, now abandoned.

(60) Provisional application No. 61/856,268, filed on Jul. 19, 2013.

(51) Int. Cl.
| | |
|---|---|
| *A61K 31/715* | (2006.01) |
| *C12N 15/117* | (2010.01) |
| *A61K 39/39* | (2006.01) |
| *A01K 67/00* | (2006.01) |
| *A61K 39/00* | (2006.01) |

(52) U.S. Cl.
CPC ............ *C12N 15/117* (2013.01); *A61K 39/39* (2013.01); *A61K 2039/55505* (2013.01); *A61K 2039/55561* (2013.01); *C12N 2310/17* (2013.01)

(58) Field of Classification Search
CPC .. C12N 15/117; C12N 2310/17; A61K 39/39; A61K 2039/55561; A61K 2039/55505
See application file for complete search history.

(56) References Cited

U.S. PATENT DOCUMENTS

| | | |
|---|---|---|
| 5,151,499 A | 9/1992 | Kameyama et al. |
| 7,408,050 B2 | 8/2008 | Kim et al. |
| 2008/0124366 A1 | 5/2008 | Ohlfest et al. |
| 2017/0039316 A1 | 2/2017 | Fofanov |

OTHER PUBLICATIONS

A. Cuesta et al. The expression profile of TLR9 mRNA and CpG ODNs immunostimulatory actions in the teleost gilthead seabream points to a major role of lymphocytes. Cell. Mol. Life Sci. 65:2091-2104, (Year: 2008).*
Krieg AM, et al., "CpG motifs in bacterial DNA trigger direct B-cell activation." Nature, Apr. 6, 1995, vol. 374, pp. 546-549.
Sato Y, et al, "Immunostimulatory DNA sequences necessary for effective intradermal gene immunization." Science, Jul. 19, 1996, vol. 273, pp. 352-354.
Wagner H., "Bacterial CpG DNA activates immune cells to signal infectious danger." Adv. Immunol., 1999, vol. 73, pp. 329-368.
Krieg A. M., "CpG motifs in bacterial DNA and their immune effects." Annu. Rev. Immunol., 2002, vol. 20, pp. 709-760.
Hemmi H, et al., "A Toll-like receptor recognizes bacterial DNA." Nature, Dec. 7, 2000, vol. 408, pp. 740-745.
Kanzler H, et al., "Therapeutic targeting of innate immunity with Toll-like receptor agonists and antagonists." Nat. Med., May 2007, vol. 13, pp. 552-559.
Klinman DM, et al., "CpG oligonucleotides as adjuvants for vaccines targeting infectious diseases." Adv. Drug Deliv. Rev., 2009, vol. 61, pp. 248-255.
Krieg A. M., "CpG still rocks! Update on an accidental drug." Nucleic Acid Ther., 2012, vol. 22, pp. 77-89.
Carrington A. C., et al., "A review of CpGs and their relevance to aquaculture." Vet. Immunol. Immunopathol., 2006, vol. 112, pp. 87-101.
Chaung HC, "CpG oligodeoxynucleotides as DNA adjuvants in vertebrates and their applications in immunotherapy." Int. Immunopharmacol., 2006, vol. 6, pp. 1586-1596.
Mutwiri G, "TLR9 agonists: immune mechanisms and therapeutic potential in domestic animals." Vet. Immunol. Immunopathol., 2012, vol. 148, pp. 85-89.
Bauer S, et al., "Human TLR9 confers responsiveness to bacterial DNA via species-specific CpG motif recognition." Proc. Natl. Acad. Sci. U. S. A., Jul. 31, 2001, vol. 98, pp. 9237-9242.
Chuang TH, et al., "Toll-like receptor 9 mediates CpG-DNA signaling." J. Leukoc. Biol., Mar. 2002, vol. 71, pp. 538-544.
Liu J, et al., "Activation of rabbit TLR9 by different CpG-ODN optimized for mouse and human TLR9." Comp Immunol. Microbiol. Infect. Dis., 2012, vol. 35, pp. 443-451.
Rankin R, et al., "CpG motif identification for veterinary and laboratory species demonstrates that sequence recognition is highly conserved." Antisense and Nucleic Acid Drug Development, 2001, vol. 11, pp. 333-340.
Weeratna RD, et al., "CpG DNA induces stronger immune responses with less toxicity than other adjuvants." Vaccine, 2000, vol. 18, pp. 1755-1762.
Stills HF, Jr., "Adjuvants and antibody production: dispelling the myths associated with Freund's complete and other adjuvants." ILAR. J., 2005, vol. 46, pp. 280-293.

(Continued)

*Primary Examiner* — Quang Nguyen
(74) *Attorney, Agent, or Firm* — Muncy, Geissler, Olds & Lowe, P.C.

(57) ABSTRACT

A method of stimulating a TLR9-activated immune response or enhancing a TLR9-activated immune response to an antigen is disclosed herein. TLR9 is the cellular receptor for CpG-ODN, and current developed CpG-ODN has low activity to rabbit TLR9. Here, the method of stimulating TLR9-activated immune response by administering an effective amount of immunogenic composition comprising an antigen and a CpG-ODN comprising GACGTT or AACGTT motif was demonstrated to have potent immunostimulatory activity to rabbit TLR9, and capable of boosting a less toxic and potent antibody response in rabbits.

5 Claims, 17 Drawing Sheets

Specification includes a Sequence Listing.

(56) References Cited

OTHER PUBLICATIONS

"Oligo Order Form", Sep. 21, 2011 (Sep. 21, 2011). Retrieved from the internet:<www.genedragon.com.tw/attachment/xlsfiles/GN-BS-110921 E.xls> on Nov. 13, 2014, p. 1.

Chuang et al. "Development of CpG-Oligodeoxynucleotides for Effective Activation of Rabbit TLR9 Mediated Immune Responses," Plos One, Sep. 30, 2014, vol. 9, No. 9, pp. 1-8.

Pezda et al. "Suppression of TLR9 Immunostimulatory Motifs in the Genome of a Gammaherpesvirus," Jun. 10, 2011, The Journal of Immunology, vol. 187, pp. 887-896.

Zhang et al., "Induction of Interleukin-6 and Interleukin-12 in bovine B lymphocytes, monocytes, and macrophages by a CpG Oligodeoxynucleotide (ODN 2059) containing the GTCGTT motif," J. Interferon & Cytokine Res. 21:871-881, 2001.

\* cited by examiner

SEQUENCE LISTING

<160> NUMBER OF SEQ ID NOS: 41

<210> SEQ ID NO 1
<211> LENGTH: 14
<212> TYPE: DNA
<213> ORGANISM: Artificial Sequence
<220> FEATURE:
<223> OTHER INFORMATION: Synthesized sequence

<400> SEQUENCE: 1
tccatgacgt tcct                                                     14

```
<210> SEQ ID NO 2
<211> LENGTH: 12
<212> TYPE: DNA
<213> ORGANISM: Artificial Sequence
<220> FEATURE:
<223> OTHER INFORMATION: Synthesized sequence

<400> SEQUENCE: 2
tcatgacgtt ct                                                          12

<210> SEQ ID NO 3
<211> LENGTH: 11
<212> TYPE: DNA
<213> ORGANISM: Artificial Sequence
<220> FEATURE:
<223> OTHER INFORMATION: Synthesized sequence

<400> SEQUENCE: 3
tctgacgttc t                                                           11

<210> SEQ ID NO 4
<211> LENGTH: 12
<212> TYPE: DNA
<213> ORGANISM: Artificial Sequence
<220> FEATURE:
<223> OTHER INFORMATION: Synthesized sequence

<400> SEQUENCE: 4
tcataacgtt ct                                                          12

<210> SEQ ID NO 5
<211> LENGTH: 12
<212> TYPE: DNA
<213> ORGANISM: Artificial Sequence
<220> FEATURE:
<223> OTHER INFORMATION: Synthesized sequence

<400> SEQUENCE: 5
tcatgacgtt cc                                                          12

<210> SEQ ID NO 6
<211> LENGTH: 12
<212> TYPE: DNA
<213> ORGANISM: Artificial Sequence
<220> FEATURE:
<223> OTHER INFORMATION: Synthesized sequence

<400> SEQUENCE: 6
tcataacgtt cc                                                          12

<210> SEQ ID NO 7
<211> LENGTH: 24
<212> TYPE: DNA
<213> ORGANISM: Artificial Sequence
<220> FEATURE:
<223> OTHER INFORMATION: Synthesized sequence

<400> SEQUENCE: 7
ccgagtacgt ggtggaatcc actg                                             24

<210> SEQ ID NO 8
<211> LENGTH: 25
<212> TYPE: DNA
<213> ORGANISM: Artificial Sequence
<220> FEATURE:
<223> OTHER INFORMATION: Synthesized sequence
```

<400> SEQUENCE: 8
ctgtagccaa attcgttgtc atacc                                    25

<210> SEQ ID NO 9
<211> LENGTH: 21
<212> TYPE: DNA
<213> ORGANISM: Artificial Sequence
<220> FEATURE:
<223> OTHER INFORMATION: Synthesized sequence

<400> SEQUENCE: 9
gtcccctcgg ctgctcgctg g                                        21

<210> SEQ ID NO 10
<211> LENGTH: 22
<212> TYPE: DNA
<213> ORGANISM: Artificial Sequence
<220> FEATURE:
<223> OTHER INFORMATION: Synthesized sequence

<400> SEQUENCE: 10
caggctgacc gcaacggctg gc                                       22

<210> SEQ ID NO 11
<211> LENGTH: 24
<212> TYPE: DNA
<213> ORGANISM: Artificial Sequence
<220> FEATURE:
<223> OTHER INFORMATION: Synthesized sequence

<400> SEQUENCE: 11
gacacggatt ggtacagagc ttcg                                     24

<210> SEQ ID NO 12
<211> LENGTH: 26
<212> TYPE: DNA
<213> ORGANISM: Artificial Sequence
<220> FEATURE:
<223> OTHER INFORMATION: Synthesized sequence

<400> SEQUENCE: 12
cttggaactc atggcctgac caacag                                   26

<210> SEQ ID NO 13
<211> LENGTH: 23
<212> TYPE: DNA
<213> ORGANISM: Artificial Sequence
<220> FEATURE:
<223> OTHER INFORMATION: Synthesized sequence

<400> SEQUENCE: 13
ctccaagtcc ctctgctctc tgg                                      23

<210> SEQ ID NO 14
<211> LENGTH: 23
<212> TYPE: DNA
<213> ORGANISM: Artificial Sequence
<220> FEATURE:
<223> OTHER INFORMATION: Synthesized sequence

<400> SEQUENCE: 14
aggcacaagg gctgtattgc ttc                                      23

<210> SEQ ID NO 15

```
<211> LENGTH: 22
<212> TYPE: DNA
<213> ORGANISM: Artificial Sequence
<220> FEATURE:
<223> OTHER INFORMATION: Synthesized sequence

<400> SEQUENCE: 15
tcgtcgttgt cgttttgtcg tt                                              22

<210> SEQ ID NO 16
<211> LENGTH: 22
<212> TYPE: DNA
<213> ORGANISM: Artificial Sequence
<220> FEATURE:
<223> OTHER INFORMATION: Synthesized sequence

<400> SEQUENCE: 16
tcgacgttgt cgttttgtcg tt                                              22

<210> SEQ ID NO 17
<211> LENGTH: 22
<212> TYPE: DNA
<213> ORGANISM: Artificial Sequence
<220> FEATURE:
<223> OTHER INFORMATION: Synthesized sequence

<400> SEQUENCE: 17
tcgtcgttga cgttttgtcg tt                                              22

<210> SEQ ID NO 18
<211> LENGTH: 22
<212> TYPE: DNA
<213> ORGANISM: Artificial Sequence
<220> FEATURE:
<223> OTHER INFORMATION: Synthesized sequence

<400> SEQUENCE: 18
tcgtcgttgt cgttttgacg tt                                              22

<210> SEQ ID NO 19
<211> LENGTH: 22
<212> TYPE: DNA
<213> ORGANISM: Artificial Sequence
<220> FEATURE:
<223> OTHER INFORMATION: Synthesized sequence

<400> SEQUENCE: 19
tgctgcttgt gcttttgtgc tt                                              22

<210> SEQ ID NO 20
<211> LENGTH: 20
<212> TYPE: DNA
<213> ORGANISM: Artificial Sequence
<220> FEATURE:
<223> OTHER INFORMATION: Synthesized sequence

<400> SEQUENCE: 20
tccatgacgt tcctgacgtt                                                 20

<210> SEQ ID NO 21
<211> LENGTH: 20
<212> TYPE: DNA
<213> ORGANISM: Artificial Sequence
<220> FEATURE:
<223> OTHER INFORMATION: Synthesized sequence

<400> SEQUENCE: 21
```
tccatgtcgt tcctgtcgtt                                                20

<210> SEQ ID NO 22
<211> LENGTH: 20
<212> TYPE: DNA
<213> ORGANISM: Artificial Sequence
<220> FEATURE:
<223> OTHER INFORMATION: Synthesized sequence

<400> SEQUENCE: 22
tccatgtcgt tcctgacgtt                                                20

<210> SEQ ID NO 23
<211> LENGTH: 20
<212> TYPE: DNA
<213> ORGANISM: Artificial Sequence
<220> FEATURE:
<223> OTHER INFORMATION: Synthesized sequence

<400> SEQUENCE: 23
tccatgacgt tcctgtcgtt                                                20

<210> SEQ ID NO 24
<211> LENGTH: 20
<212> TYPE: DNA
<213> ORGANISM: Artificial Sequence
<220> FEATURE:
<223> OTHER INFORMATION: Synthesized sequence

<400> SEQUENCE: 24
tccatgagct tcctgagctt                                                20

<210> SEQ ID NO 25
<211> LENGTH: 20
<212> TYPE: DNA
<213> ORGANISM: Artificial Sequence
<220> FEATURE:
<223> OTHER INFORMATION: Synthesized sequence

<400> SEQUENCE: 25
tccatgagct tcctgtcgtt                                                20

<210> SEQ ID NO 26
<211> LENGTH: 20
<212> TYPE: DNA
<213> ORGANISM: Artificial Sequence
<220> FEATURE:
<223> OTHER INFORMATION: Synthesized sequence

<400> SEQUENCE: 26
tccatgacgt tcctgtgctt                                                20

<210> SEQ ID NO 27
<211> LENGTH: 16
<212> TYPE: DNA
<213> ORGANISM: Artificial Sequence
<220> FEATURE:
<223> OTHER INFORMATION: Synthesized sequence

<400> SEQUENCE: 27
tccatgacgt tcctgt                                                    16

<210> SEQ ID NO 28
<211> LENGTH: 11
<212> TYPE: DNA

```
<213> ORGANISM: Artificial Sequence
<220> FEATURE:
<223> OTHER INFORMATION: Synthesized sequence

<400> SEQUENCE: 28
ttcctgtcgt t                                                          11

<210> SEQ ID NO 29
<211> LENGTH: 12
<212> TYPE: DNA
<213> ORGANISM: Artificial Sequence
<220> FEATURE:
<223> OTHER INFORMATION: Synthesized sequence

<400> SEQUENCE: 29
tccatgacgt tc                                                         12

<210> SEQ ID NO 30
<211> LENGTH: 12
<212> TYPE: DNA
<213> ORGANISM: Artificial Sequence
<220> FEATURE:
<223> OTHER INFORMATION: Synthesized sequence

<400> SEQUENCE: 30
catgacgttc ct                                                         12

<210> SEQ ID NO 31
<211> LENGTH: 10
<212> TYPE: DNA
<213> ORGANISM: Artificial Sequence
<220> FEATURE:
<223> OTHER INFORMATION: Synthesized sequence

<400> SEQUENCE: 31
catgacgttc                                                            10

<210> SEQ ID NO 32
<211> LENGTH: 10
<212> TYPE: DNA
<213> ORGANISM: Artificial Sequence
<220> FEATURE:
<223> OTHER INFORMATION: Synthesized sequence

<400> SEQUENCE: 32
tatgacgttt                                                            10

<210> SEQ ID NO 33
<211> LENGTH: 11
<212> TYPE: DNA
<213> ORGANISM: Artificial Sequence
<220> FEATURE:
<223> OTHER INFORMATION: Synthesized sequence

<400> SEQUENCE: 33
tcatgacgtc t                                                          11

<210> SEQ ID NO 34
<211> LENGTH: 11
<212> TYPE: DNA
<213> ORGANISM: Artificial Sequence
<220> FEATURE:
<223> OTHER INFORMATION: Synthesized sequence

<400> SEQUENCE: 34
catgacgttc t                                                          11
```

<210> SEQ ID NO 35
<211> LENGTH: 10
<212> TYPE: DNA
<213> ORGANISM: Artificial Sequence
<220> FEATURE:
<223> OTHER INFORMATION: Synthesized sequence

<400> SEQUENCE: 35
tcgacgttct                                                                 10

<210> SEQ ID NO 36
<211> LENGTH: 10
<212> TYPE: DNA
<213> ORGANISM: Artificial Sequence
<220> FEATURE:
<223> OTHER INFORMATION: Synthesized sequence

<400> SEQUENCE: 36
atgacgttct                                                                 10

<210> SEQ ID NO 37
<211> LENGTH: 24
<212> TYPE: DNA
<213> ORGANISM: Artificial Sequence
<220> FEATURE:
<223> OTHER INFORMATION: Synthesized sequence

<400> SEQUENCE: 37
tcgtcgtttt gtcgttttgt cgtt                                                 24

<210> SEQ ID NO 38
<211> LENGTH: 12
<212> TYPE: DNA
<213> ORGANISM: Artificial Sequence
<220> FEATURE:
<223> OTHER INFORMATION: Synthesized sequence

<400> SEQUENCE: 38
tcatgtcgtt ct                                                              12

<210> SEQ ID NO 39
<211> LENGTH: 12
<212> TYPE: DNA
<213> ORGANISM: Artificial Sequence
<220> FEATURE:
<223> OTHER INFORMATION: Synthesized sequence

<400> SEQUENCE: 39
tcatatcgtt ct                                                              12

<210> SEQ ID NO 40
<211> LENGTH: 12
<212> TYPE: DNA
<213> ORGANISM: Artificial Sequence
<220> FEATURE:
<223> OTHER INFORMATION: Synthesized sequence

<400> SEQUENCE: 40
tcatgtcgtt cc                                                              12

<210> SEQ ID NO 41
<211> LENGTH: 12
<212> TYPE: DNA
<213> ORGANISM: Artificial Sequence
<220> FEATURE:

```
<223> OTHER INFORMATION: Synthesized sequence

<400> SEQUENCE: 41
tcatatcgtt cc                                                              12
```

METHOD OF STIMULATING TLR9-ACTIVATED IMMUNE RESPONSE

CROSS-REFERENCE TO RELATED APPLICATION

This application is a continuation of U.S. patent application Ser. No. 14/906,150, filed on Jan. 19, 2016, in the United States Patent and Trademark Office, which claims the benefit of U.S. Provisional Application No. 61/856,268, filed on Jul. 19, 2013, the disclosure of which is incorporated herein in its entirety by reference.

BACKGROUND OF THE INVENTION

1. Field of the Invention

The present invention generally relates to a method for stimulating TLR9-activated immune response.

2. Description of the Related Art

CpG-oligodeoxynucleotides (CpG-ODN) are potent immune stimuli and toll-like receptor 9 (TLR9) is their cellular receptor (1-5). Activation of TLR9 by CpG-ODN can result in a number of immunological effects including increasing of a T helper (Th) 1 polarized cytokine productions, up-regulation of major histocompatibility complex (MHC) co-stimulatory molecules, as well as activation and enhance B cell proliferation to increase antibody productions. Because of these potent immunostimulatory effects, CpG-ODNs are being investigated for a broad range of applications from immunotherapies for allergy, cancer and infectious diseases in human to be utilized as adjuvant in different species (6-11).

In general, a CpG-ODN contains 18-24 phosphorothioated deoxynucleotides in length with one or more copies of CpG-deoxynucleotides containing hexamer motifs (CpG-motifs), and its immunostimulatory activity is dependent on the number of CpG-motifs, and the position, spacing, and surrounding bases of the CpG-motifs. The immunostimulatory activity of a CpG-ODN could be different in different species. Current knowledge is that this species-different property is determined by the nucleotide context of the CpG-motifs within the CpG-ODN. For example, CpG-ODN containing GTCGTT motif generates higher immune responses in human and different domestic animals than those with GACGTT motif; in contrast, the latter are more potent in activation of murine cells (3, 4). The species-different activity of a CpG-ODN is due to a different extent of TLR9 activation in different species (12, 13).

A previous study showed that in contrast to human (h) TLR9 and mouse (m) TLR9, the rabbit (rab) TLR9 has a more broad ligand recognition profile to CpG-ODN with either GTCGTT motifs or GACGTT motifs; however, CpG-ODN current developed for activation human or mouse cells have low activity to rabTLR9 (14). These results were consistent with the observation reported by Rankin et al. In which, they showed that no preference of CpG-ODN with GTCGTT or GACGTT motif was seen for activation of rabbit cells (15). Thus, it is indispensable to develop a CpG-ODN, as a TLR9-activated adjuvant, having high activity to rabTLR9 to facilitate antibody response in rabbits, thereby increasing antibody generation in rabbits.

REFERENCES

The disclosure of following references is incorporated herein in its entirety by reference.

1. Krieg A M, Yi A K, Matson S, Waldschmidt T J, Bishop G A, Teasdale R, Koretzky G A and Klinman D M (1995) CpG motifs in bacterial DNA trigger direct B-cell activation. Nature 374:546-549
2. Sato Y, Roman M, Tighe H, Lee D, Corr M, Nguyen M D, Silverman G J, Lotz M, Carson D A and Raz E (1996) Immunostimulatory DNA sequences necessary for effective intradermal gene immunization. Science 273:352-354
3. Wagner H (1999) Bacterial CpG DNA activates immune cells to signal infectious danger. Adv. Immunol. 73:329-368
4. Krieg A M (2002) CpG motifs in bacterial DNA and their immune effects. Annu. Rev. Immunol. 20:709-760
5. Hemmi H, Takeuchi O, Kawai T, Kaisho T, Sato S, Sanjo H, Matsumoto M, Hoshino K, Wagner H, Takeda K and Akira S (2000) A Toll-like receptor recognizes bacterial DNA. Nature 408:740-745
6. Kanzler H, Barrat F J, Hessel E M and Coffman R L (2007) Therapeutic targeting of innate immunity with Toll-like receptor agonists and antagonists. Nat. Med. 13:552-559
7. Klinman D M, Klaschik S, Sato T and Tross D (2009) CpG oligonucleotides as adjuvants for vaccines targeting infectious diseases. Adv. Drug Deliv. Rev. 61:248-255
8. Krieg A M (2012) CpG still rocks! Update on an accidental drug. Nucleic Acid Ther. 22:77-89
9. Carrington A C and Secombes C J (2006) A review of CpGs and their relevance to aquaculture. Vet. Immunol. Immunopathol. 112:87-101
10. Chaung H C (2006) CpG oligodeoxynucleotides as DNA adjuvants in vertebrates and their applications in immunotherapy. Int. Immunopharmacol. 6:1586-1596
11. Mutwiri G (2012) TLR9 agonists: immune mechanisms and therapeutic potential in domestic animals. Vet. Immunol. Immunopathol. 148:85-89
12. Bauer S, Kirschning C J, Hacker H, Redecke V, Hausmann S, Akira S, Wagner H and Lipford G B (2001) Human TLR9 confers responsiveness to bacterial DNA via species-specific CpG motif recognition. Proc. Natl. Acad. Sci. U. S. A 98:9237-9242
13. Chuang T H, Lee J, Kline L, Mathison J C and Ulevitch R J (2002) Toll-like receptor 9 mediates CpG-DNA signaling. J. Leukoc. Biol. 71:538-544
14. Liu J, Xu C, Liu Y L, Matsuo H, Hsieh R P, Lo J F, Tseng P H, Yuan C J, Luo Y, Xiang R and Chuang T H (2012) Activation of rabbit TLR9 by different CpG-ODN optimized for mouse and human TLR9. Comp Immunol Microbiol. Infect. Dis. 35:443-451
15. Rankin R, Pontarollo R, Ioannou X, Krieg A M, Hecker R, Babiuk L A and Van Drunen Littel-van den Hurk S (2001) CpG motif identification for veterinary and laboratory species demonstrates that sequence recognition is highly conserved. Antisense and Nucleic Acid Drug Development, 11 (5) (2001), pp. 333-340
16. Weeratna R D, McCluskie M J, Xu Y and Davis H L (2000) CpG DNA induces stronger immune responses with less toxicity than other adjuvants. Vaccine 18:1755-1762
17. Stills H F, Jr. (2005) Adjuvants and antibody production: dispelling the myths associated with Freund's complete and other adjuvants. ILAR. J. 46:280-293

SUMMARY OF THE INVENTION

Therefore, it is a primary objective of the present invention to provide a method for stimulating TLR9-activated immune response, thereby boosting antibody in a host may be more effective.

To achieve the foregoing objective, the present invention provides a method of stimulating a TLR9-activated immune response or enhancing a TLR9-activated immune response to an antigen, comprising administering to a host an effective amount of a immunogenic composition comprising an antigen and a CpG-oligodeoxynucleotide (CpG-ODN) comprising GACGTT or AACGTT motif in 12-14 nucleotides and selected from the group consisting of the nucleotide sequences of SEQ ID NO: 1, SEQ ID NO: 2, SEQ ID NO: 4, SEQ ID NO: 5 and SEQ ID NO: 6.

Preferably, the host may be mouse or rabbit.

Preferably, the administering may comprise subcutaneous injection.

Preferably, a ratio between the antigen and the CpG-ODN of the immunogenic composition is in a range from 3:50 to 10:50.

Preferably, the immunogenic composition further comprises an aluminum hydroxide gel.

Preferably, a concentration of the aluminum hydroxide gel may be in a range of 0.2-1% (V/V).

The method for stimulating TLR9-activated immune response according to embodiments of the present invention may have the following advantages:

(1) The method according to embodiments of the present invention may effectively activate TLR9-mediated immune response, such as production of IL-6, IL-8, IFN-α and IgM, in hosts, e.g. mice and rabbits.

(2) The method according to embodiments of the present invention may induce humoral immune response with less adverse effects, for instance, inflammation, leukocyte infiltration and granuloma, comparing to conventional CFA/IFA adjuvant.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The properties and effects of the present invention will now be described in more details hereinafter with reference to the accompanying drawings that show various embodiments of the invention as follows.

DETAILED DESCRIPTION OF THE PREFERRED EMBODIMENTS

Figure 1A:
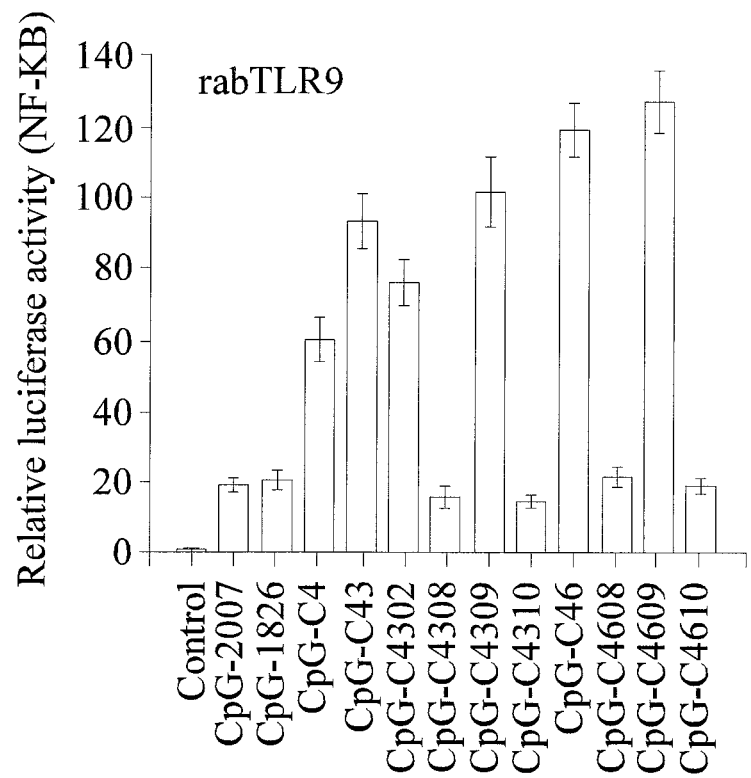
FIGS. 1A-1B are schematic views of activation of TLR9s by CpG-ODN developed for rabbits. 293 cells were transfected with expression vector for rabTLR9 (FIG. 1A), and human, mouse and rabbit TLR9 as indicated plus a NF-κB controlled luciferase-reporter gene, and treated with 2 uM of CpG-ODN for 7 h (FIG. 1B). Relative luciferase activities were then determined Data shown represent mean±SD (n=3). The sequences of CpG-ODN used in this study were shown in the right table of FIG. 1A.

The technical content of the present invention will become apparent by the detailed description of the following embodiments and the illustration of related drawings as follows.

Definitions

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

"Adjuvant" means any substance that increases the humoral or cellular immune response to an antigen. Adjuvants are generally used to accomplish two objectives: The slow the release of antigens from the injection site, and the stimulation of the immune system.

"Antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

"Antigen" or "immunogen" refers to any substance that stimulates an immune response. The term includes killed, inactivated, attenuated, or modified live bacteria, viruses, or parasites. The term antigen also includes polynucleotides, polypeptides, recombinant proteins, synthetic peptides, protein extract, cells (including tumor cells), tissues, polysaccharides, or lipids, or fragments thereof, individually or in any combination thereof. The term antigen also includes antibodies, such as anti-idiotype antibodies or fragments thereof, and to synthetic peptide mimotopes that can mimic an antigen or antigenic determinant (epitope).

"Buffer" means a chemical system that prevents change in the concentration of another chemical substance, e.g., proton donor and acceptor systems serve as buffers preventing marked changes in hydrogen ion concentration (pH). A further example of a buffer is a solution containing a mixture of a weak acid and its salt (conjugate base) or a weak base and its salt (conjugate acid).

"Cellular immune response" or "cell mediated immune response" is one mediated by T-lymphocytes or other white blood cells or both, and includes the production of cytokines, chemokines and similar molecules produced by activated T-cells, white blood cells, or both.

"Dose" refers to a vaccine or immunogenic composition given to a host. A "first dose" or "priming vaccine" refers to the dose of such a composition given on Day 0. A "second dose" or a "third dose" refers to an amount of such composition given subsequent to the first dose, which may or may not be the same vaccine or immunogenic composition as the first dose.

"Excipient" refers to any component of a vaccine that is not an antigen.

"Immune response" in a host refers to the development of a humoral immune response, a cellular immune response, or a humoral and a cellular immune response to an antigen. Immune responses can usually be determined using standard immunoassays and neutralization assays, which are known in the art.

"Immunologically effective amount" or "effective amount to produce an immune response" of an antigen is an amount sufficient to induce an immunogenic response in the recipient with toxicity. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain. The immune response may comprise, without limitation, induction of cellular and/or humoral immunity. As will be pointed out below, the exact amount required will vary from host to host, depending on the species, age, and general condition of the host, the severity of the condition being treated, and the particular macromolecule of interest, mode of administration, and the like. An appropriate "effective" amount in any individual case may be determined by one of ordinary skill in the art using routine experimentation.

"Immunogenic" means evoking an immune or antigenic response. Thus an immunogenic composition would be any composition that induces an immune response.

"Administering" refers to the introduction of a substance, such as an immunogenic composition, into a host by at least subcutaneous, intramuscular, transcutaneous, intradermal, intraperitoneal, intraocular, and intravenous administration.

"Host" refers to any animal for which the administration of an adjuvant composition is desired. It includes mammals and non-mammals, including primates, livestock, companion animals, laboratory test animals, captive wild animals, ayes (including in ova), reptiles, and fish. Thus, this term includes but is not limited to monkeys, humans, swine; cattle, sheep, goats, equines, mice, rats, guinea pigs, hamsters, rabbits, felines, canines, chickens, turkeys, ducks, other poultry, frogs, and lizards. Preferably, the host is mouse or rabbit.

Material and Methods

Reagents and Antibodies

CpG-ODNs were purchased from Invitrogen, or Genomics Biosci and Tech (New Taipei, Taiwan). Ovalbumin, and aluminum hydroxide gel were purchased from InvivoGen. Fruend's complete adjuvant and incomplete adjuvant were purchased from Thermo Scientific. Luciferase assay reagents were purchased from Promega.

Animal Care

New Zealand white rabbits and C57/B6J mice were maintained and handled in accordance with the guidelines of the Institutional Animal Care and Use Committee of National Health Research Institutes.

TLR9 Activation Assays

Rabbit, human, and mouse TLR9 expression constructs were generated as previously reported (14). To perform TLR9 activation assays, 293 cells were grown in Dulbecco's minimum essential medium (DMEM) supplemented with 10% fetal bovine serum, plated on 24-well plates and allowed to adhere overnight. These cells were co-transfected using PolyJet (SignaGen) with TLR9 expression vector, β-galactosidase plasmid, and a NF-κB driven luciferase reporter plasmid, and treated with 2 μM of various CpG-ODN as indicated on next day for 7 h. The cells were lysed and luciferase activity in each sample was determined. Relative luciferase activities were calculated as fold induction compared to an unstimulated control. The data are expressed as the means±SD (n=3).

RT-PCR Analysis of Cytokine Inductions

Splenocytes were prepared from rabbit spleens and maintained in RPMI medium supplemented with 10% fetal bovine serum. For analysis of cytokine inductions, cells were treated with 2 μM of CpG-ODN for 4 h. Total RNA were isolated from samples with a RNeasy mini kit (Qiagen) following the manufacturer's protocol. First strand cDNA libraries were then synthesized from the collected total RNA samples using a SuperScript™ preamplification kit (Invitrogen), and PCR amplifications were performed using an Expand HI Fid PCR kit (Roche). The primers used in the embodiment of the present invention were listed below in Table 1. PCR products were visualized by electrophoresis on a 1% agarose gel after staining with ethidium bromide.

TABLE 1

| PCR primers used in the embodiment of the present invention | | | SEQ ID |
|---|---|---|---|
| GAPDH | Forward | 5'-CCGAGTACGTGGTGGAATCCACTG-3' | NO: 7 |
| | Reverse | 5'-CTGTAGCCAAATTCGTTGTCATACC-3' | NO: 8 |
| IL-6 | Forward | 5'-GTCCCCTCGGCTGCTCGCTGG-3' | NO: 9 |
| | Reverse | 5'-CAGGCTGACCGCAACGGCTGGC-3' | NO: 10 |
| IL-8 | Forward | 5'-GACACGGATTGGTACAGAGCTTCG-3' | NO: 11 |
| | Reverse | 5'-CTTGGAACTCATGGCCTGACCAACAG-3' | NO: 12 |
| IFN-α | Forward | 5'-CTCCAAGTCCCTCTGCTCTCTGG-3' | NO: 13 |
| | Reverse | 5'-AGGCACAAGGGCTGTATTGCTTC-3' | NO: 14 |

Cell Proliferation Assays

Proliferation of spleen cells were measured by CellTiter 96 AQ$_{ueous}$ Non-Radioactive Cell Proliferation (MTS) Assay according to manufacturer's instructions (Promega, Wis., USA). Briefly, rabbit spleen cells ($1 \times 10^5$/well) were treated with 2 uM of CpG-OND for 48 h. MTS/PMS solutions were added into each well for 2 h. The absorbencies at 490 nm were measured by an Envision Alpha Multilabel Reader (PerkinElmer).

ELISA Assay for Cytokine and Total IgM Productions

Rabbit or mouse splenocyte ($1 \times 10^6$/ml) were treated with 2 μM of CpG-ODN for 2 days. The cell culture medium was collected for measurement of cytokine and IgM inductions. The total rabbit IgM were measured by Rabbit IgM ELISA Kit (GenWay Biotech, San Diego, Calif.), and mouse cytokines and IgM were measured with ELISA kits from eBiosciences (San Diego, Calif.) according to manufacturer's instruction.

Anti-OVA Antibody Measurement

Ovabumin was dissolved in ELISA Coating Buffer (eBioscience, San Diego, Calif.) and coated (2 μg/well) onto a 96-well ultra-clear polypstyrene microtiter plate (Basic Life, Taipei, Taiwan) overnight at 4° C. The plate was washed four times with 200 μl of wash solution (1×PBS and 0.05% Tween 20) and blocked with 1× assay diluent (eBioscience) for 1 h at room temperature. After four washes, 100 μl of diluted serum were added and incubated overnight at 4° C. Subsequently, after washings five times, 100 μl of 1/5000 diluted biotin-conjugated affinity purified anti-rabbit IgG (KPL Inc., Gaithersburg, Md.) was added, and the mixtures were incubated for 1 h. After being washed, 100 μl/well of 1/500 diluted Avidin-HRP (eBioscience) were added and incubated for 30 minutes. After four washes, 100 μl of TMB (eBioscience) was added and developed. The reaction was stopped by adding of 50 μl of 2N $H_2SO_4$. The absorbance was determined at 450 nm on Envision Alpha Multilabel Reader (PerkinElmer).

Histology Analysis

For histology analysis, the isolated tissues were immersed in 10% of formalin. These samples were then embedded in paraffin wax and sections were hematoxylin-eosin (HE) stained.

Statistical Analysis

Groups of data are expressed as mean±SD. Statistical analyses were performed using Student's t-test. All groups were from three or more independent experiments. $p<0.05$ was considered statistically significant.

Results

Figure 4:
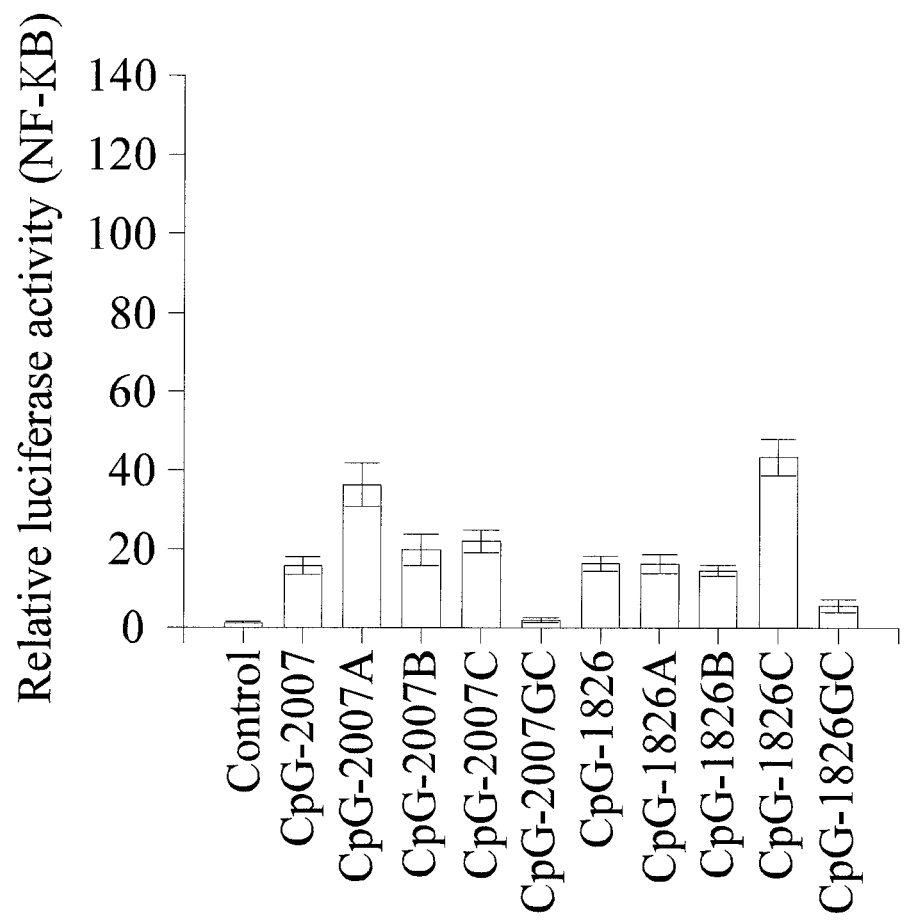
FIG. 4 is a schematic view of activation of rabTLR9 by CpG-ODN derived from CpG-2007 and CpG-1826. CpG-2007 and CpG-1826 developed for activation of human and mouse cells respectively were shown to have low activities to rabTLR9. These two CpG-ODNs were modified to contain different combinations of GACGTT and GTCGTT motif in their sequence as shown in the right table. 293 cells were transfected with expression vector for rabTLR9 and a NF-κB controlled luciferase-reporter gene and then treated with 2 μM of these CpG-ODNs. Luciferase activities induced in these cells were determined. Data shown represent mean±SD (n=3). The results indicated that the CpG-1826C had a better activity in activation of rabTLR9.

At first, inventors of the present invention were curious about what will be the activity of a CpG-ODN to rabTLR9, if this CpG-ODN contains both of the GTCGTT and GACGTT motifs in it as described in the section of Description of the Related Art. CpG-2007 and CpG-1826 which were optimized for human and mouse cells contain 3 copies of GTCGTT motifs and 2 copies of GACGTT motifs, respectively. They were modified into different CpG-ODN with these two different types of CpG-motifs together in the same CpG-ODN. The activities of these CpG-ODNs were investigated with a cell-based rabTLR9 activation assay in which the activation of rabTLR9 was measured by luciferase reporter activity. Interestingly, inventors of the present invention found that a CpG-1826-C with a copy of GACGTT motif following with a copy of GTCGTT motif had better activities than its parental CpG-2007, CpG-1826 and other modified CpG-ODN (FIG. 4). The CpG-ODNs tested in FIG. 4 according to the embodiment of the present invention were listed below in Table 2.

TABLE 2

| Sequences used in FIG. 4 | | |
|---|---|---|
| CpG-ODNs | Sequence | SEQ ID |
| CpG-2007 | TCGTCGTTGTCGTTTTGTCGTT | NO: 15 |
| CpG-2007-A | TCGACGTTGTCGTTTTGTCGTT | NO: 16 |
| CpG-2007-B | TCGTCGTTGACGTTTTGTCGTT | NO: 17 |
| CpG-2007-C | TCGTCGTTGTCGTTTTGACGTT | NO: 18 |
| CpG-2007-GC | TGCTGCTTGTGCTTTTGTGCTT | NO: 19 |
| CpG-1826 | TCCATGACGTTCCTGACGTT | NO: 20 |
| CpG-1826-A | TCCATGTCGTTCCTGTCGTT | NO: 21 |
| CpG-1826-B | TCCATGTCGTTCCTGACGTT | NO: 22 |
| CpG-1826-C | TCCATGACGTTCCTGTCGTT | NO: 23 |
| CpG-1826-GC | TCCATGAGCTTCCTGAGCTT | NO: 24 |

Figure 5:
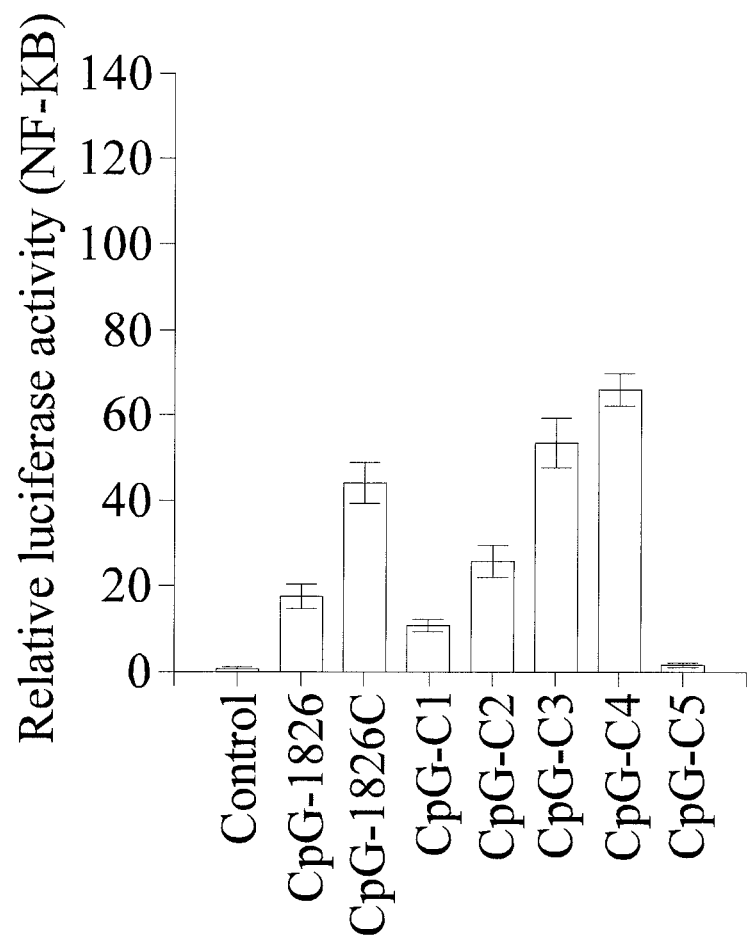
FIG. 5 is a schematic view of activation of rabTLR9 by CpG-ODN derived from CpG-1826C. CpG-1826C was further modified into different CpG-ODN with sequences as shown in the right table to investigate the molecular determinant of its activity to rabTLR9. 293 cells transfected with expression vector for rabTLR9 and a NF-κB controlled luciferase-reporter gene were treated with these CpG-ODN. Relative luciferase activities were determined. Data shown represent mean±SD (n=3). The results indicated that a CpG-C4 with 14 deoxynucleotides in length had a better activity to rabTLR9.

In an attempt to develop optimized CpG-ODN for effective activation of rabTLR9 and immune responses in rabbits, inventors of the present invention asked if a copy of GACGTT and a copy of GTCGTT motif in a CpG-ODN is indeed required for a strong activity. The CpG-1826-C was further modified into several different CpG-ODN with the CpG-deoxynucleotides reversed in the two different types of motif, or with the N-terminal or C-terminal GACGTT or GTCGTT motif deleted. Among these CpG-ODNs, a CpG-C4 generated a best activity to rabTLR9. This CpG-ODN contains 14 phosphorothiolated deoxynucleotides in length, and is a truncated form of the CpG-1826-C with the C-terminal GTCGTT motif deleted. This suggested the C-terminal GTCGTT motif is not required for a strong activity of rabTLR9 (FIG. 5). Moreover, the increased activity from CpG-1826C, CpG-C3 and CpG-C4 which contain reduced length from 20, 16 to 14 phosphorothiolated deoxynucleotides, respectively, led inventors speculate that the length of a CpG-ODN may be critical for strong activation of rabTLR9. The CpG-ODNs tested in FIG. 5 according to the embodiment of the present invention were listed below in Table 3.

TABLE 3

Sequences used in FIG. 5

| CpG-ODNs | Sequence | SEQ ID |
| --- | --- | --- |
| CpG-1826 | TCCATGACGTTCCTGACGTT | NO: 20 |
| CpG-1826-C | TCCATGACGTTCCTGTCGTT | NO: 23 |
| CpG-C1 | TCCATGAGCTTCCTGTCGTT | NO: 25 |
| CpG-C2 | TCCATGACGTTCCTGTGCTT | NO: 26 |
| CpG-C3 | TCCATGACGTTCCTGT | NO: 27 |
| CpG-C4 | TCCATGACGTTCCT | NO: 1 |
| CpG-C5 | TTCCTGTCGTT | NO: 28 |

Figure 6:
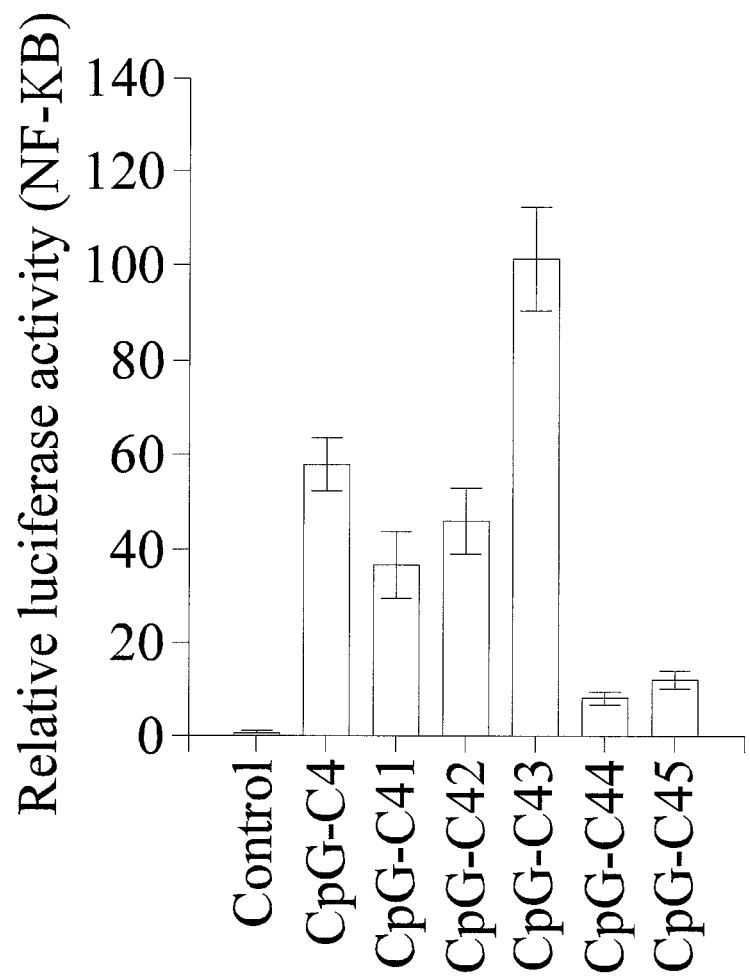
FIG. 6 is a schematic view of activation of rabTLR9 by CpG-ODN derived from CpG-C4. CpG-C4 was further modified into different CpG-ODN with sequences as shown in the right table. 293 cells transfected with expression vector for rabTLR9 and a NF-κB controlled luciferase-reporter gene were treated with these CpG-ODN. Relative luciferase activities were determined. Data shown represent mean±SD (n=3). The results indicated that a CpG-C43 with a length of 12 deoxynucleotides had a better activity to rabTLR9.
Figure 7:
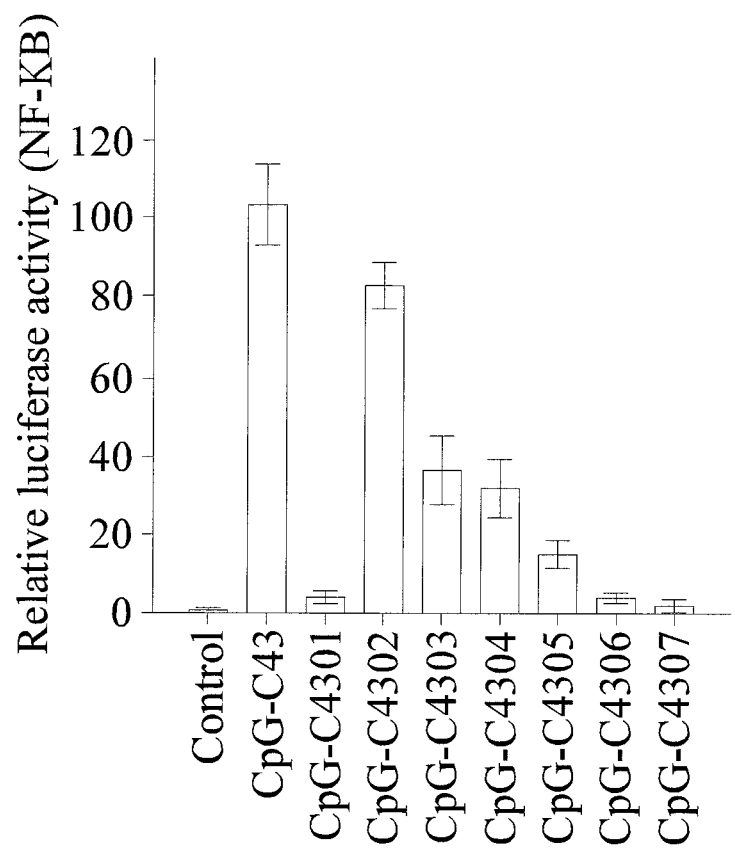
FIG. 7 is a schematic view of activation of rabTLR9 by CpG-ODN derived from CpG-C43. CpG-C43 was further modified into different CpG-ODN with different lengths from 8-12 deoxynucleotides as shown in the right table to determine the optimal length for activation of rabTLR9. 293 cells transfected with expression vector for rabTLR9 and a NF-κB controlled luciferase-reporter gene were treated with these CpG-ODN. Relative luciferase activities were determined. Data shown represent mean±SD (n=3). The results indicated that CpG-C43 with a length of 12 deoxynucleotides had a strongest activity to rabTLR9, and the CpG-C4302 with a length of 11 deoxynucleotides remaining has good activity to rabTLR9.

Inventors of the present invention further reduced the length and changed the 5' and 3' phosphorothiolated deoxynucleotides to modify the CpG-ODN. Results from cell-based activation assay indicated that CpG-ODN contain 12 phosphorothiolated deoxynucleotides in length with a GACGTT motif or AACGTT motif such as the CpG-43, CpG-4309, CpG-46 and CpG-4609 have strong activities to the rabbit TLR9, whereas those with GTCGTT motif or ATCGTT motif such as the CpG-C4308, CpG-C4310, CpG-C4608 and CpG-C4610 have weak activities (FIG. 6 and FIG. 1A). CpG-ODN contains 11 phosphorothiolated deoxynucleotides such as the CpG-4302 remaining has good activity to rabTLR9 although not as good as the CpG-43, but further trimming of the length reduced the activity dramatically (FIG. 7). The CpG-ODNs tested in FIGS. 6, 7 and 1 according to the embodiments of the present invention were listed below in Tables 4, 5 and 6, respectively.

TABLE 4

Sequences used in FIG. 6

| CpG-ODNs | Sequence | SEQ ID |
| --- | --- | --- |
| CpG-C4 | TCCATGACGTTCCT | NO: 1 |
| CpG-C41 | TCCATGACGTTC | NO: 29 |
| CpG-C42 | CATGACGTTCCT | NO: 30 |
| CpG-C43 | TCATGACGTTCT | NO: 2 |
| CpG-C44 | CATGACGTTC | NO: 31 |
| CpG-C45 | TATGACGTTT | NO: 32 |

TABLE 5

Sequences used in FIG. 7

| CpG-ODNs | Sequence | SEQ ID |
| --- | --- | --- |
| CpG-C43 | TCATGACGTTCT | NO: 2 |
| CpG-C4301 | TCATGACGTCT | NO: 33 |
| CpG-C4302 | TCTGACGTTCT | NO: 3 |
| CpG-C4303 | CATGACGTTCT | NO: 34 |
| CpG-C4304 | TCGACGTTCT | NO: 35 |
| CpG-C4305 | ATGACGTTCT | NO: 36 |
| CpG-C4306 | TGACGTTCT | |
| CpG-C4307 | TGACGTCT | |

TABLE 6

Sequences used in FIG. 1

| CpG-ODNs | Sequence | SEQ ID |
| --- | --- | --- |
| CpG-2006 | TCGTCGTTTTGTCGTTTTGTCGTT | NO: 37 |
| CpG-2007 | TCGTCGTTGTCGTTTTGTCGTT | NO: 15 |
| CpG-1826 | TCCATGACGTTCCTGACGTT | NO: 20 |
| CpG-C4 | TCCATGACGTTCCT | NO: 1 |
| CpG-C43 | TCATGACGTTCT | NO: 2 |
| CpG-C4302 | TCTGACGTTCT | NO: 3 |
| CpG-C4308 | TCATGTCGTTCT | NO: 38 |
| CpG-C4309 | TCATAACGTTCT | NO: 4 |
| CpG-C4310 | TCATATCGTTCT | NO: 39 |
| CpG-C46 | TCATGACGTTCC | NO: 5 |
| CpG-C4608 | TCATGTCGTTCC | NO: 40 |
| CpG-C4609 | TCATAACGTTCC | NO: 6 |
| CpG-C4610 | TCATATCGTTCC | NO: 41 |

Figure 1B:
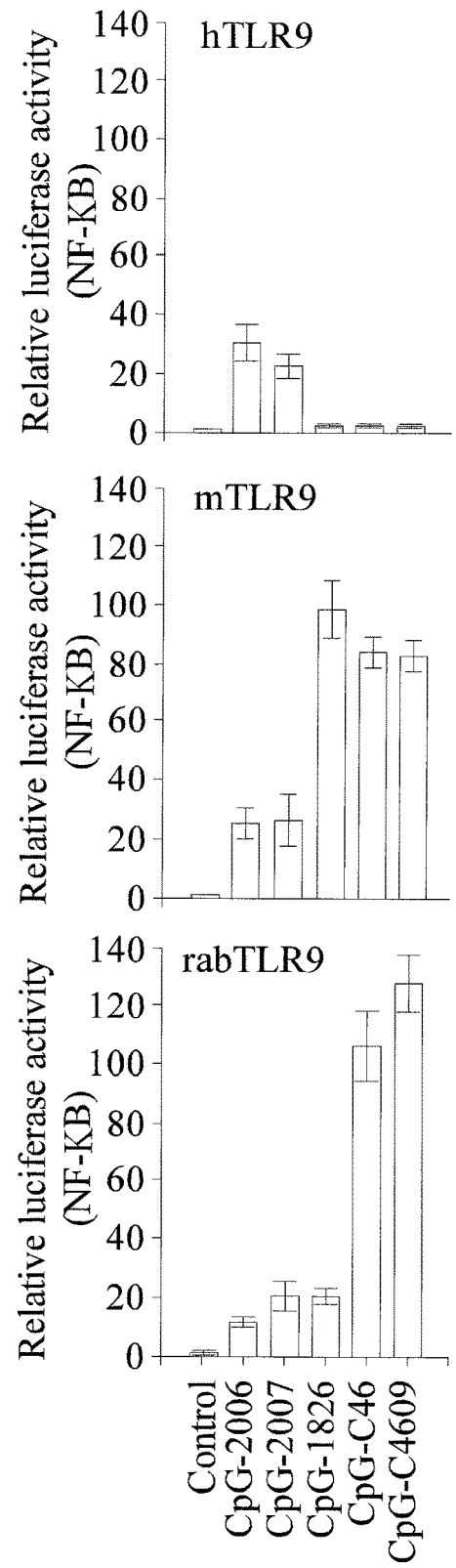
Figure 2A:
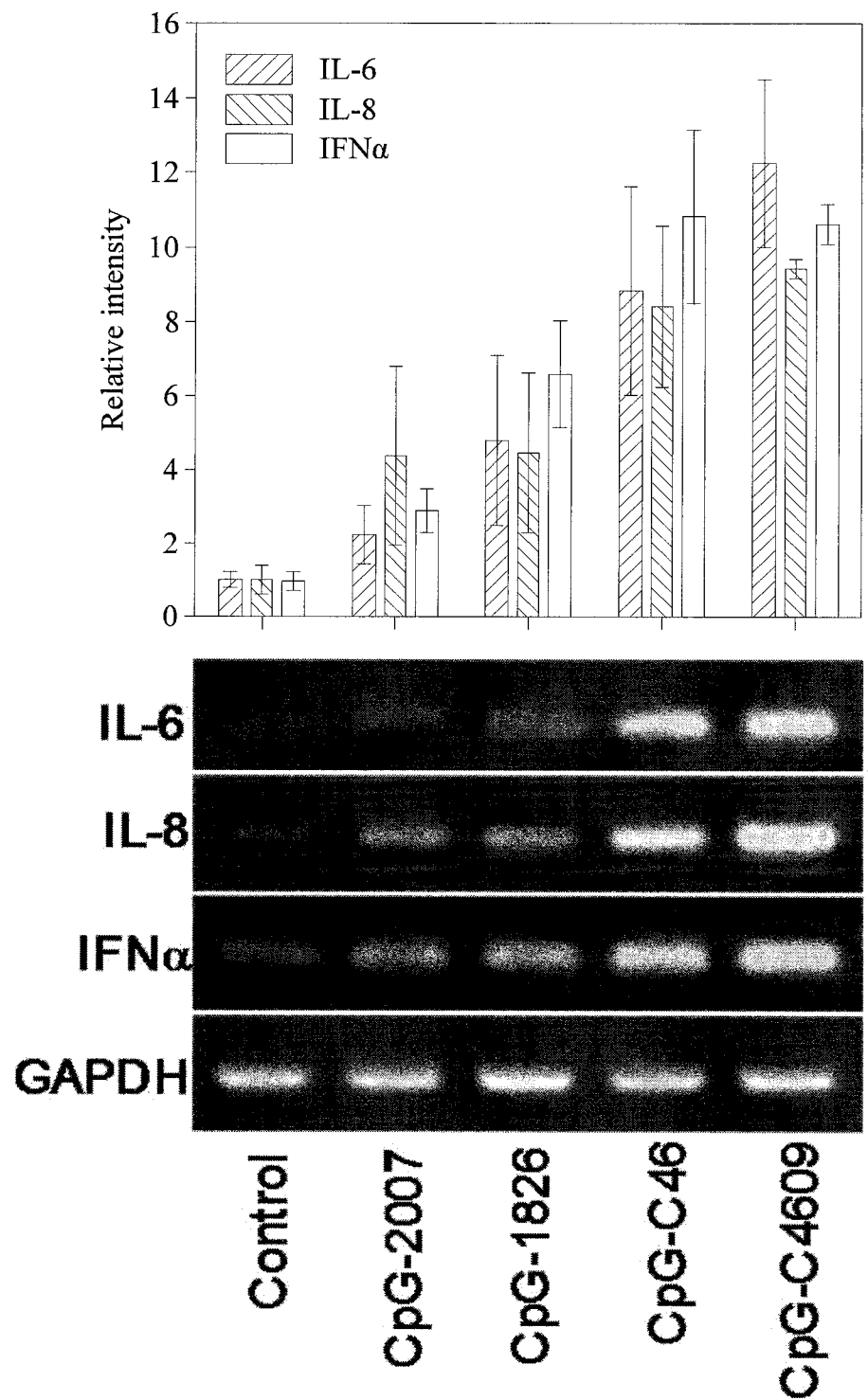
FIGS. 2A-2C are schematic views of activation of immune responses in rabbit splenocytes by CpG-ODN developed for rabbits. Rabbit splenocytes were stimulated with 2 uM of different CpG-ODN. Induction of cytokines were analyzed by RT-PCR (FIG. 2A). Productions of IgM were determined by ELISA (FIG. 2B). Proliferations of splenocytes were measured by MTS assay (FIG. 2C). Data shown represent mean±SD (n=3)
Figure 2B:
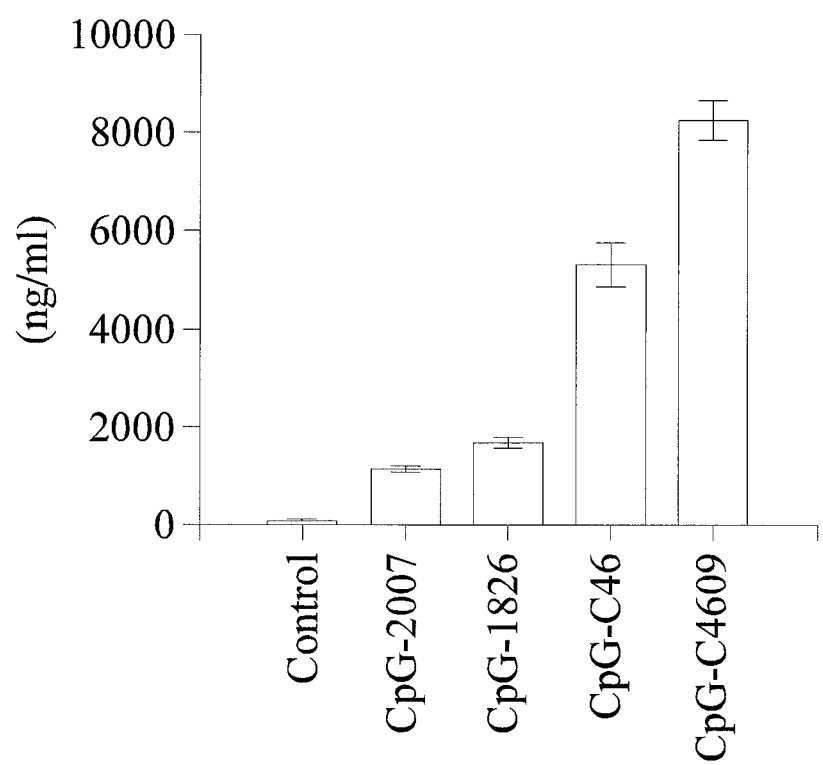
Figure 2C:
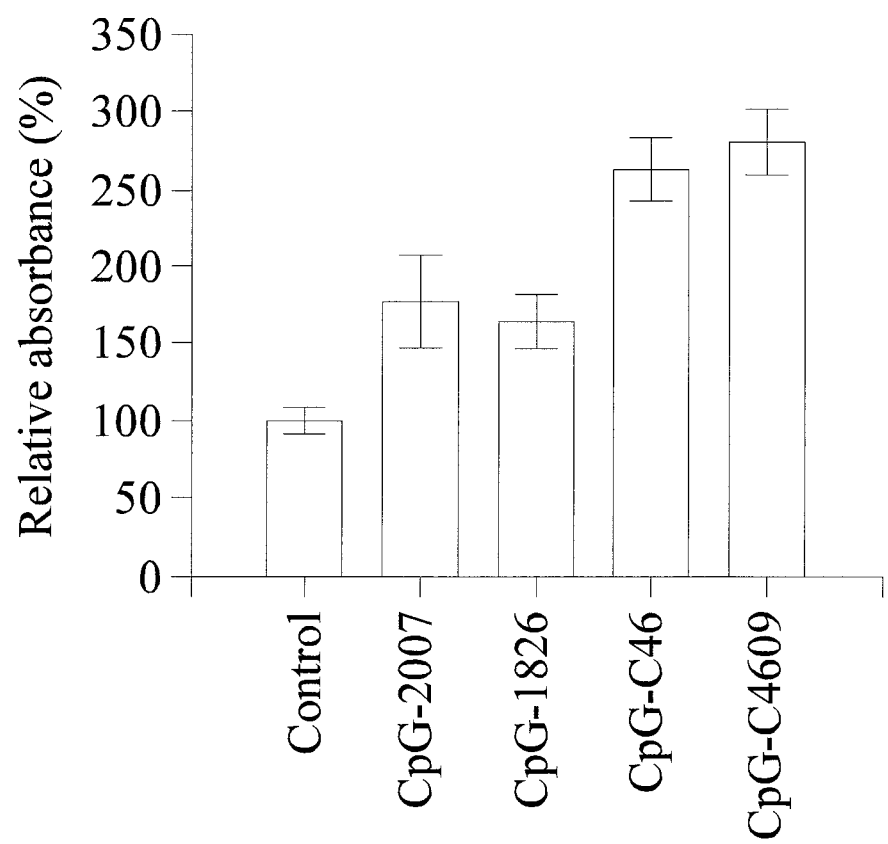
Figure 8:
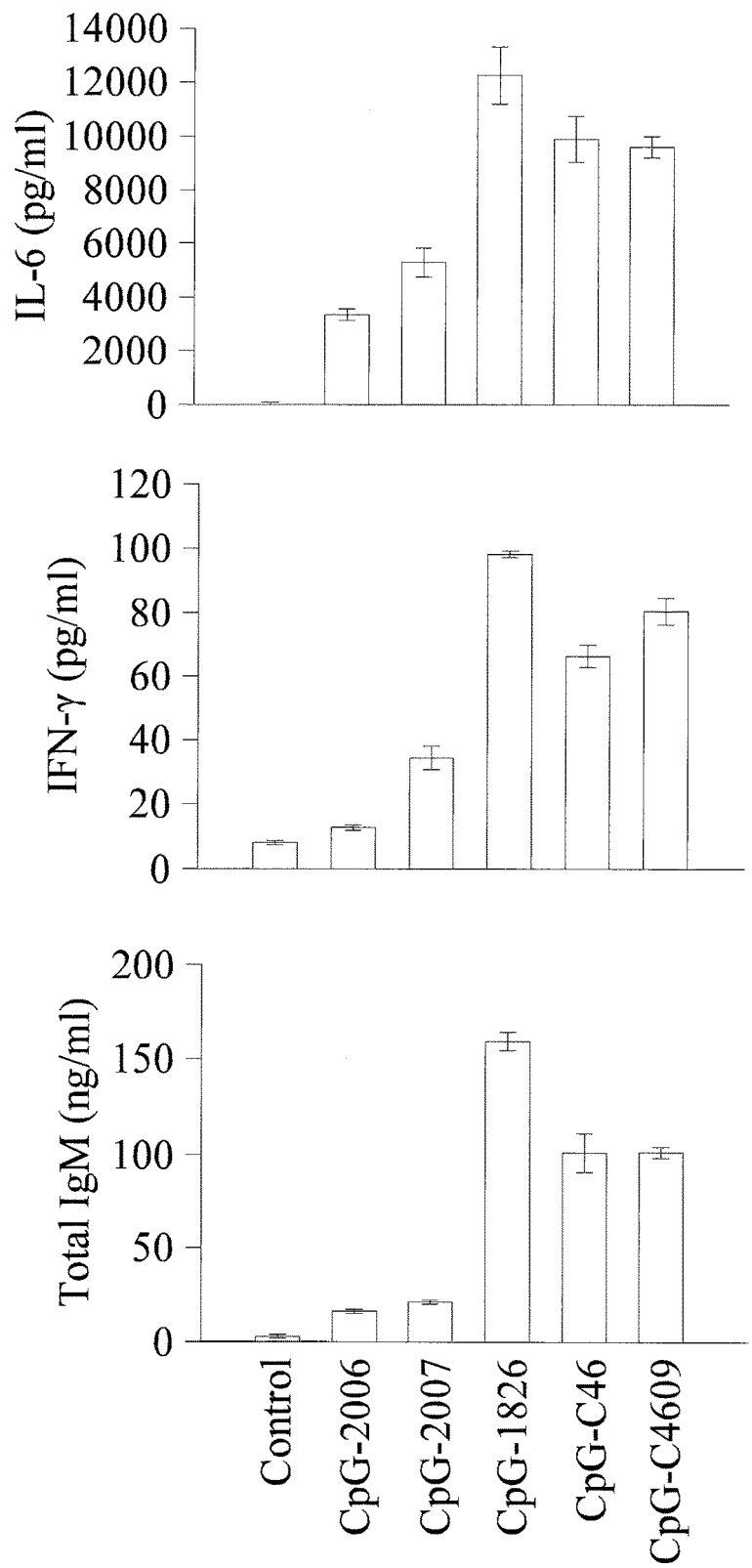
FIG. 8 is a schematic view of activation of mouse splenocytes by CpG-ODN developed for rabbits. Mouse splenocytes were stimulated with 2 μM of different CpG-ODN optimized for human (CpG-2006 and CpG-2007), mouse (CpG-1826), and developed for rabbit (CpG-46 and CpG-4609. Induction of (a) IL-6, (b) IFN-γ, and productions of (c) IgM were determined by ELISA. Data shown represent mean±SD (n=3).
Figure 9A:
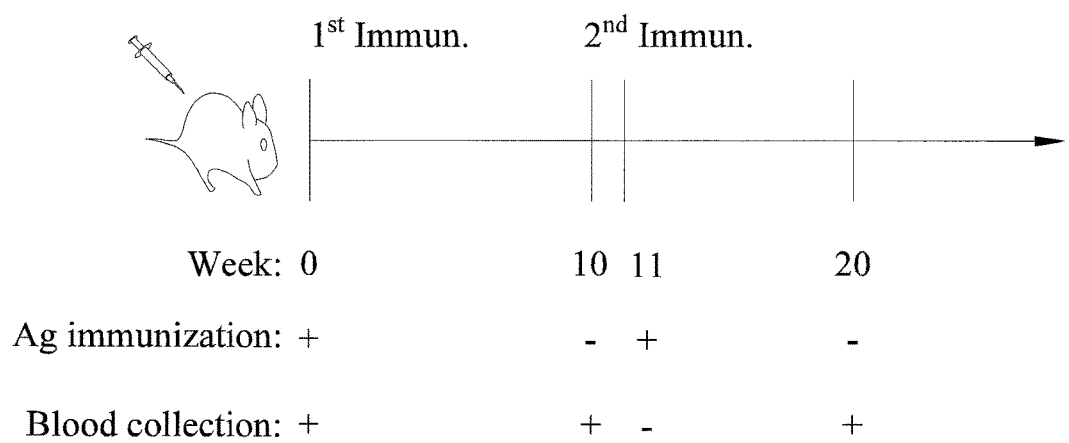
FIGS. 9A-9B are schematic views of efficiency of the developed CpG-ODN in boosting antibody productions in mice. A 10 days interval schedule as shown was adopted for each cycle of immunization and serum collection from C57/B6J mice (FIG. 9A). 1 µg of OVA was formulated with/without 5 µg of CpG-ODN in PBS for each mouse. Anti-OVA antibody titers were measure with ELISA (FIG. 9B).
Figure 9B:
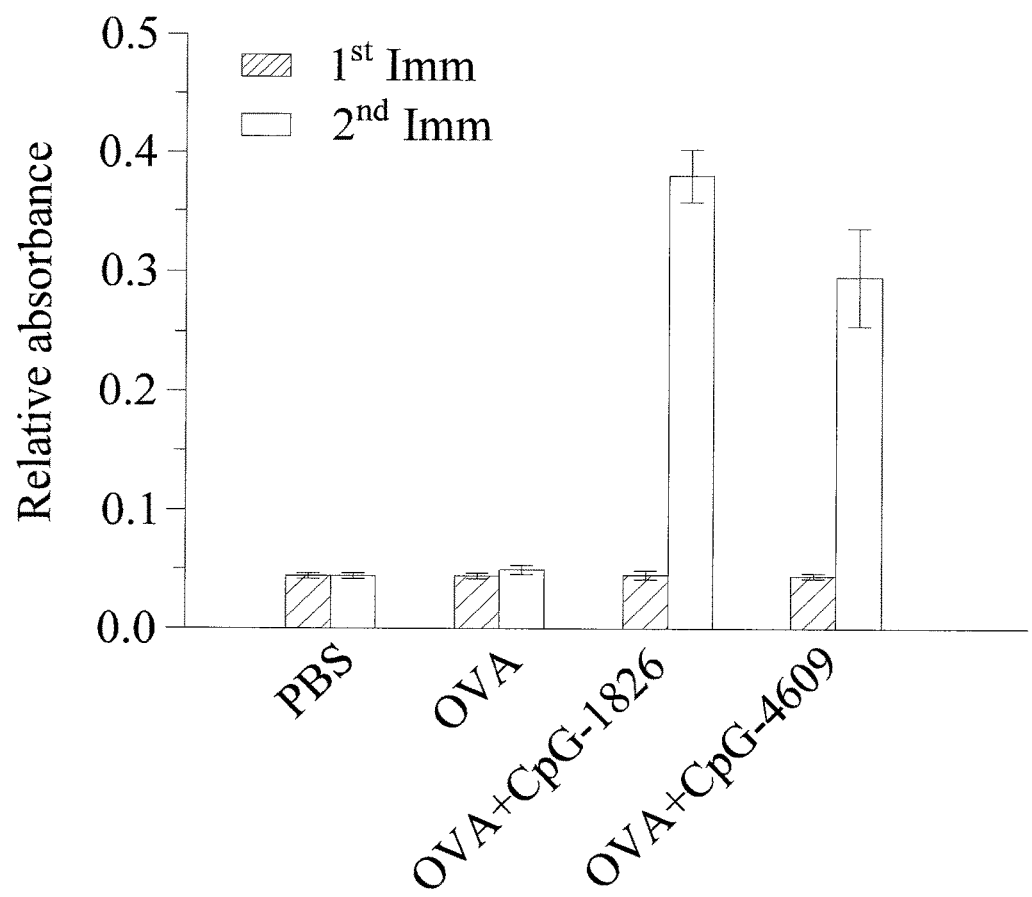

The CpG-C46 and CpG-C4609, one contains GACGTT motif and the other contains AACGTT motif were picked up for further studies to compare their activities with CpG-2006, CpG-2007 (optimized for human cells) and CpG-1826 (optimized for mouse cells) for hTLR9, mTLR9 and rabTLR9 activations. Compared to these three CpG-ODN, the CpG-C46 and CpG-C4609 were much more potent in activation of rabTLR9 and better activities than the CpG- 2006 and CpG-2007 to activate mTLR9, but had no activity to hTLR9 (FIG. 1B). The immunostimulatory activities of these CpG-ODNs were further investigated with splenocytes isolated from rabbits. Cytokines productions induced in these cells were analyzed by RT-PCR. Cell proliferations were measured by MTS assay and IgM productions were determined by ELISA assay. In line with their activities in the cell-based rabTLR9 activation assays, the CpG-C46 and CpG-C4609 had better activities than the CpG-2007 and CpG-1826 to activate IL-6, IL-8, IFN-α inductions (FIG. 2A), and IgM productions in splenocytes (FIG. 2B). In addition, CpG-C46 and CpG-C4609 also had better activities to increase proliferation of the rabbit splenocytes (FIG. 2C). The activities of CpG-C46, and CpG-C4609 to induce immune responses in mouse splenocytes were further compared with other CpG-ODN. Similar to their activities in the mTLR9 activation assays (FIG. 1B), the CpG-C46 and CpG-C4609 had better activities than the CpG-2006 and -2007 to induced IL-6, IFN-γ and IgM productions in these cells, although the activities were not as strong as the CpG-1826 (FIG. 8). In line with this, the CpG-4609 also effectively activated antigen specific antibody production in mice (FIG. 9).

Figure 3A:
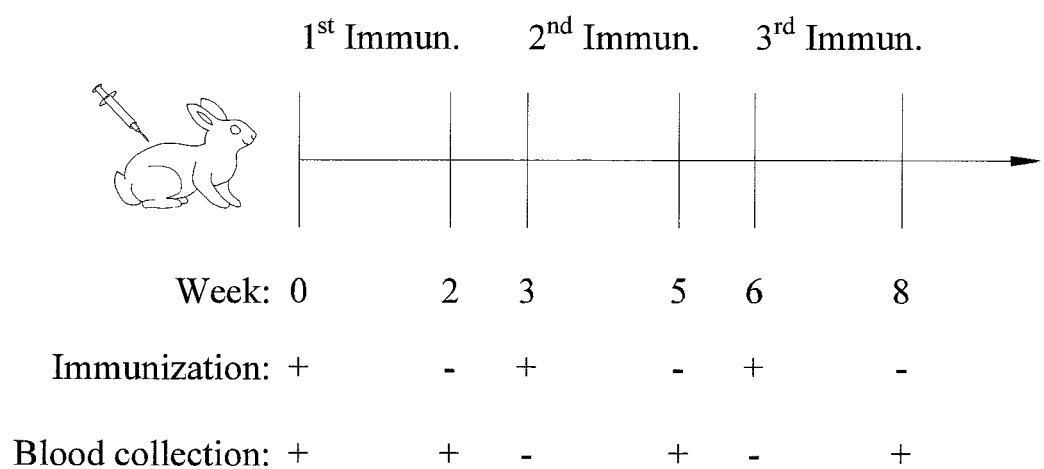
FIGS. 3A-3E are schematic views of efficacy and safety of the developed CpG-ODN in boosting antibody productions in rabbits. A three weeks interval schedule as shown was adopted for each cycle of immunization and serum collection (FIG. 3A). 10 μg of OVA was formulated with 50 μg of CpG-ODN in PBS or CFA/IFA (FIG. 3B), 3 μg of OVA was formulated with 50 μg of CpG-ODN in PBS or CFA/IFA to determine the efficacy and safety of CpG-C4609 as adjuvant in boosting antibody productions (FIG. 3C). Anti-OVA antibody titers were measure with ELISA. Upper panels: subcutaneous tissues at the injection sites were examined at the second day after injection of different combinations of antigen and adjuvant as indicated (FIG. 3D). Lower panels: HE staining of sections taken from these tissues. Upper panels: an example of granuloma appeared on CFA/IFA injected rabbit (FIG. 3E). Lower panels: HE staining of section taken from this granuloma.
Figure 3B:
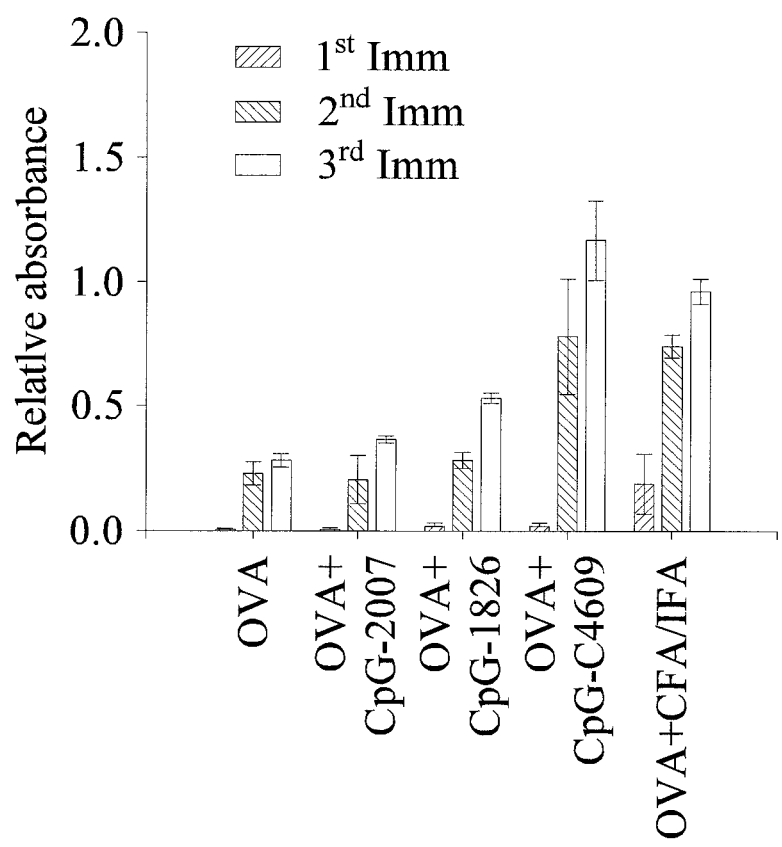
Figure 3C:
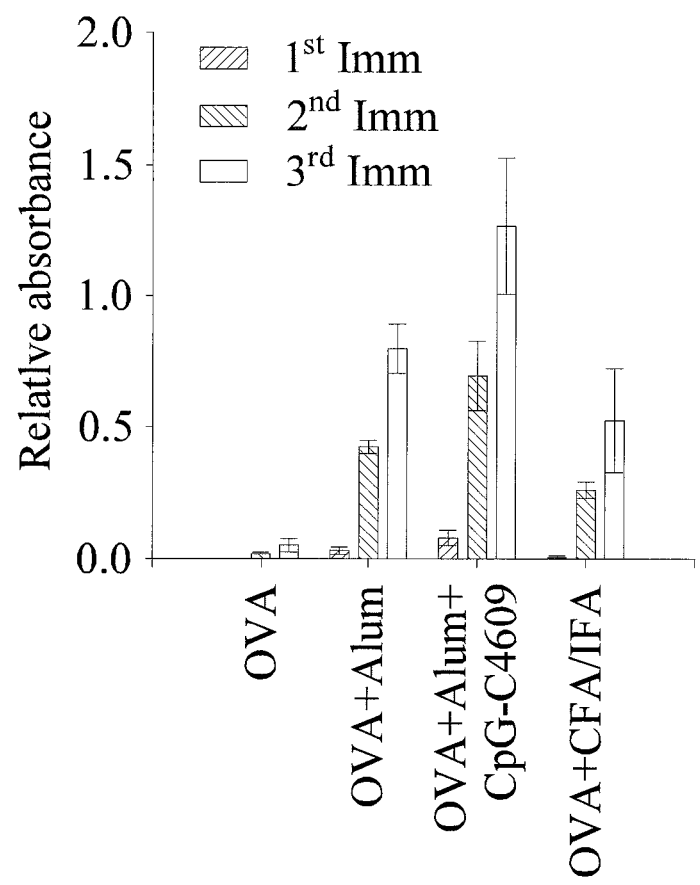
Figure 3D:
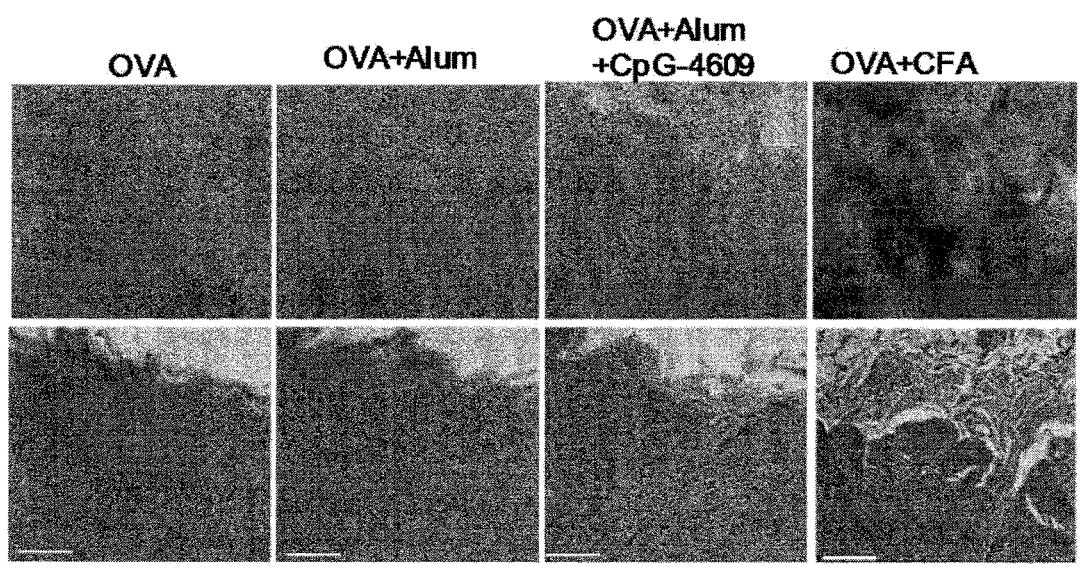
Figure 3E:
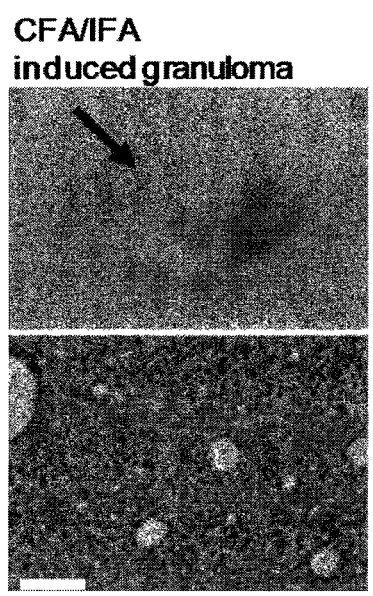

In addition to be raised as pet, rabbits are commonly used in laboratories for production of antibodies. Freud's adjuvant is widely utilized for effectively boosting antibody productions in this animal. However, this adjuvant has strong adverse effect to causes inflammatory responses and lesions of tissues around the injection sites (16, 17). Therefore, complete Freud's adjuvant (CFA) is used only for the first immunization and incomplete Freud's adjuvant (IFA) is used for subsequent immunizations. To determine the in vivo immunostimulatory activity of these developed CpG-ODNs, inventors of the present invention further investigated their capability as adjuvant to boost antibody productions in rabbits. Inventors of the present invention compared the safety and efficacy of CpG-C4609 with CFA/IFA in boosting antibody productions as well. Ovalbumin (OVA), a conventional protein antigen, was subcutaneously (sc) injected into rabbits after mixed with these adjuvants. A three weeks interval as shown in FIG. 3A was adopted for each cycle of immunization and blood collection. In an embodiment, a ratio between the antigen used and the CpG-ODN may be in a range from 3:50 to 10:50, preferably in a range from 5:50 to 10:50, most preferably 7:50 to 10:50. In a preferred embodiment, when mixed with 10 μg of OVA, the antibody responses elicited by 50 μg of CpG-C4609 in PBS were as good as that elicited by CFA/IFA (FIG. 3B). In another embodiment, a concentration of the aluminum hydroxide gel may be in a range of 0.1-2% (V/V), preferably in a range of 0.2-1.2% (V/V), most preferably in a range of 0.2-1% (V/V). In a preferred embodiment, when mixed with 3 μg of OVA, the antibody responses induced by 50 μg of CpG-C4609 in 1% of aluminum hydroxide gel (alum) were better that that elicited by alum alone or by CFA/IFA (FIG. 3C). Adverse effect of these adjuvants was further examined. At the $2^{nd}$ day after sc injection, massive lesions and inflammation appeared at the subcutaneous tissues of the CFA injection sites. In contrast, much less or no tissue damages were seen at the alum or the alum mixed CpG-C4609 injection sites (FIG. 3D, upper panel). Similarly, histopathologic analysis with HE staining revealed leukocytes infiltration and damage of the subcutaneous tissues at the CFA injection sites, but not the areas injected with alum and the alum mixed CpG-C4609 (FIG. 3D, lower panel). Moreover, granuloma as shown in FIG. 3E was sometimes seen at the CFA/IFA injection sites, but this was not seen at the alum or the alum mixed CpG-C4609 injection sites. These indicated that the CpG-4609 is less toxic than the CFA/IFA, and is a safer adjuvant to elicit potent antibody response in rabbits.

Overall, in the embodiments of the present invention, inventors of the present invention have developed a type of CpG-ODN for effectively targeting TLR9 to activate immune responses in rabbits. These CpG-ODNs comprise a GACGTT motif or a AACGTT motif, which are the CpG-motifs to effectively activate mTLR9 (3, 4). In this regard, it is consistent with that both mouse and rabbit are rodents, and the mTLR9 and rabTLR9 are phylogenetically closely related to each other. This type of CpG-ODN is unique and distinct from the current developed CpG-ODN for human and mice in their length. A short length of 11-12 deoxynucleotides is preferable for effectively activation of rabTLR9. This indicates that in addition to the CpG-motifs, the length of a CpG-ODN is also a critical factor for its different activities in different species. CpG-ODN optimized for human and mice are being investigated for various therapeutic applications in human, and being used as an agent to activate immune responses and boost antigen specific antibody productions in mice, but are less effective in domestic animals (6-11). The results in the present invention also suggested that it is possible to target TLR9 from individual species to optimize CpG-ODN for that species, and both of the CpG-motif and the length are important factors to be considered when develop CpG-ODN for different species.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A method of stimulating a TLR9-activated immune response or enhancing a TLR9-activated immune response to an antigen, comprising administering to a rabbit or a mouse an effective amount of an immunogenic composition comprising an antigen and a CpG-oligodeoxynucleotide (CpG-ODN) comprising a GACGTT motif or a AACGTT motif; wherein said CpG-ODN consists of the sequence of SEQ ID NO: 1, SEQ ID NO: 2, SEQ ID NO: 4, SEQ ID NO: 5, or SEQ ID NO: 6.

2. The method of claim 1, wherein the administering comprises subcutaneous injection.

3. The method of claim 1, wherein a ratio between the antigen and the CpG-ODN of the immunogenic composition is in a range from 3:50 to 10:50.

4. The method of claim 1, wherein the immunogenic composition further comprises an aluminum hydroxide gel.

5. The method of claim 4, wherein a concentration of the aluminum hydroxide gel is in a range of 0.2-1% (V/V).

* * * * *